(12) United States Patent
Bast et al.

(10) Patent No.: US 6,440,114 B1
(45) Date of Patent: Aug. 27, 2002

(54) DISPOSABLE ABSORBENT ARTICLE HAVING FECAL MANAGEMENT LAYER

(75) Inventors: Tim Bast, Schwalbach; Jorg Muller, Karben, both of (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/554,544

(22) PCT Filed: Nov. 16, 1998

(86) PCT No.: PCT/US98/24387

§ 371 (c)(1),
(2), (4) Date: May 15, 2000

(87) PCT Pub. No.: WO99/25293

PCT Pub. Date: May 27, 1999

(30) Foreign Application Priority Data

Nov. 14, 1909 (DE) ................................ PCT/US97/20701
Nov. 14, 1997 (DE) ................................ PCT/US97/20840

(51) Int. Cl.⁷ ............................................... A61F 13/15
(52) U.S. Cl. ................... 604/385.01; 604/384; 604/378
(58) Field of Search ........................... 604/385.01, 384, 604/378, 385.19, 385.26

(56) References Cited

U.S. PATENT DOCUMENTS

| 4,676,786 | A | * | 6/1987 | Nishino ....................... 604/378 |
| H1511 | H | * | 12/1995 | Chappell et al. ............. 604/383 |
| 5,941,863 | A | * | 8/1999 | Guidotti et al. .............. 604/378 |
| 6,132,409 | A | * | 10/2000 | Vogt et al. ................... 604/348 |
| 6,222,092 | B1 | * | 4/2001 | Hansen et al. ............... 604/378 |
| 6,241,714 | B1 | * | 6/2001 | Raidel et al. ................ 604/378 |

* cited by examiner

*Primary Examiner*—John G. Weiss
*Assistant Examiner*—Jacqueline F Stephens
(74) *Attorney, Agent, or Firm*—Jeffrey R. Moore; David M. Weirich; Ken K. Patel

(57) ABSTRACT

The present invention is a disposable absorbent article having a liquid pervious topsheet, a backsheet joined to the topsheet, and a fecal management member positioned between the topsheet and the backsheet. The fecal management member includes a backing and a sheet of fibers. The sheet of fibers has anchor portions in the backing at spaced bonding locations and has arcuate portions of the sheet projecting from the backing between bonding locations.

19 Claims, 6 Drawing Sheets

_DISPOSABLE ABSORBENT ARTICLE HAVING FECAL MANAGEMENT LAYER_

FIELD OF THE INVENTION

The present invention relates to articles which absorb and/or contain bodily exudates, including disposable absorbent articles such as diapers, adult incontinence products, sanitary napkins and the like. More particularly, the invention relates to disposable absorbent articles which have the capacity to retain low-viscosity fecal material away from the skin of the wearer, in order to reduce leakage and make it easier to clean the wearer when the soiled disposable absorbent article is removed.

BACKGROUND OF THE INVENTION

Disposable absorbent articles such as diapers and adult incontinence product are well known in the art. Such disposable absorbent articles collect and retain urine and fecal material deposited thereon by the wearer.

To date, most attempts in the art to handle the urine and fecal material collected and retained in the disposable absorbent article have been directed to handling urine. Dealing with fecal material collected by the disposable absorbent article is simply more difficult than dealing with urine, due to the complex rheology of low-viscosity material.

Exemplary of the urine handling prior art are several attempts to provide disposable absorbent articles having a first topsheet which faces towards and contacts the body of the wearer, and a secondary topsheet under the first topsheet, which either absorbs urine, or transfers the urine to an underlying core for storage until the disposable absorbent article is removed from the wearer.

Typically, the first topsheet and secondary topsheet have different material properties. The secondary topsheet may have a smaller pore size than the first topsheet, to assist in transfer of the urine through the topsheet. The first topsheet may be hydrophobic and more resilient when wetted than the secondary topsheet, in order to pass fluids through the first topsheet to the secondary topsheet.

In yet another attempt in the prior art, the disposable absorbent article has a first topsheet, secondary topsheet and core. The secondary topsheet consists essentially of meltblown hydrophilic fibers and has a pore size greater than the pore size of the core. This arrangement allegedly allows the secondary topsheet to rapidly receive multiple liquid insults and distribute the liquid in the X-Y plane prior to absorption by the core. In yet another attempt, improved vertical wicking capability for urine has been allegedly achieved using inflated cellulose fibers which are free of a surface finish or are crosslinked to one another.

In another attempt in the prior art, an absorbent core suitable for acquiring and containing liquids such as urine in a particularly effective and efficient manner comprises multiple layers. The first layer, which is closest to the wearer, comprises hydrophilic fibrous material and has an acquisition zone of a relatively lower average density than other portions of this layer, in order to quickly acquire discharged liquids. Below the first layer is a liquid handling layer comprising a resilient, low density high void volume material that is moisture insensitive in order to rapidly acquire liquid insults into itself through the acquisition zone and distribute these liquids throughout the liquid handling layer to a storage layer. The storage layer comprises a combination of fibrous material and discrete particles of absorbent gelling material, and allows the liquid handling layer to be drained of the liquids it has acquired, so that the liquid handling layer may have sufficient capacity to acquire and distribute subsequent loadings of liquids.

Examples of such attempts in the prior art include U.S. Pat. No. 4,047,531 issued Sep. 13, 1977 to Karami; U.S. Pat. No. 4,798,603 issued Jan. 17, 1989 to Meyer et al.; U.S. Pat. No. 5,037,409 issued Aug. 6, 1991 to Chen et al.; U.S. Pat. No. 5,124,197 issued Jun. 23, 1992 to Bernardin et al.; and U.S. Pat. No. 5,134,007 issued Jul. 28, 1992 to Reising et al.

Of course, absorbent gelling materials are also now well known in the prior art for their urine handling capability. Absorbent gelling materials are polymeric materials capable of absorbing large quantities of fluids, such as urine, and retaining such absorbed fluids under moderate pressure. The effectiveness of the absorbent gelling materials is quite dependent upon the form, position, and weight percentage of the absorbent gelling materials which are incorporated into the core of the disposable absorbent article.

Recent attempts have been made in the art to provide absorbent gelling materials which have the ability to swell against pressure. These teachings allege to provide the advantage that the absorbent gelling materials absorb fluid under actual pressures exerted by the body during use. Yet other teachings in the art provide absorbent gelling materials having a particular free swell rate and absorbency under load. Alleged advantages of such an absorbent gelling materials are lower volume and mass with approximately the same absorbent capacity, the ability to rapidly absorb a discharged liquid under pressures typically encountered during use, and the ability to retain the absorbed liquid under pressures typically encountered during use.

Examples of such attempts in the prior art include U.S. Pat. No. 5,147,343 issued Sep. 15, 1992 to Kellenberger and U.S. Pat. No. 5,149,335 issued Sep. 22, 1992 to Kellenberger et al.

However, all of these attempts to handle urine do little, if anything, to improve handling of low-viscosity fecal material which may also be present in the disposable absorbent article. Attempts to deal with fecal material include providing a first topsheet which conforms closely to the wearer and has an aperture. The aperture is hopefully registered with the anal opening, so that fecal material passes therethrough into a void space. The first topsheet may comprise various elastic panels in order to closely conform to the skin of the wearer, and/or may have linear elastic strands. Improvements have been made in this area of the prior art, such as optimizing the material properties of the first topsheet. Such optimization makes the first topsheet more comfortable to the wearer and allows a single disposable absorbent article to fit a larger range of sizes of wearers.

Yet other attempts have been made in this area of the prior art to provide an absorbent core with a hole therein, in order to receive the fecal material. The hole may be oblate shaped, so that it is longer and narrower than the aperture in the first topsheet, or may be diamond shaped. The hole in the core may be positioned below an aperture which has elastic strips around its edge.

Improvements to this genre of the prior art disposable absorbent articles also include the addition of spacers. Spacers may be interposed between the first topsheet and the core, in order to ensure a void space is present to receive the fecal material.

Yet other attempts have been made in this genre of the prior art to provide barriers which limit the movement of fecal material to particular portions of the disposable absorbent article. The barriers limit the contact of the fecal material to a lesser portion of the skin of the wearer, than a comparable disposable absorbent article which has no barriers.

Still other attempts in the prior art provide barrier leg cuffs which are upstanding from the plane of the topsheet. The barrier leg cuffs prevent fecal material from breaching the perimeter of the disposable absorbent article.

Examples of such attempts to handle fecal material include U.S. Pat. No. 4,892,536 issued Jan. 9, 1990 to DesMarais et al.; U.S. Pat. No. 4,909,803 issued Mar. 20, 1990 to Aziz et al.; U.S. Pat. No. 4,968,312 issued Nov. 6, 1990 to Khan; commonly assigned U.S. Pat. No. 4,990,147 issued Feb. 5, 1991 to Freeland; commonly assigned U.S. Pat. No. 5,037,416 issued Aug. 6, 1991 to Allen et al.; U.S. Pat. No. 5,062,840 issued Nov. 5, 1991 to Holt et al., commonly assigned U.S. Pat. No. 5,171,236 issued Dec. 15, 1992 to Dreier et al.; and European Patent Application 0,355,740 A2 published Feb. 28, 1990 to Enloe.

However, none of these attempts to handle fecal material solve the problem of low-viscosity fecal material which is prevalent in younger children, particularly those who are breast fed. Low-viscosity fecal material easily migrates within the disposable absorbent article under the influences of gravity and motion or pressure by the wearer.

The migration of the fecal material often moves it towards the perimeter of the disposable absorbent article, increasing the likelihood of leakage. The migration of the fecal material also smears it against the skin of the wearer, making cleanup more difficult. In order to clean the wearer, the caretaker must wipe the entire area of the skin which has encountered the fecal material and typically has to deal with a relatively large soiled area.

One attempt in the art to handle low-viscosity fecal material is found in U.S. patent application Ser. No. 08/076, 713 filed Jun. 11, 1993 in the name of Roe. This application is a disposable absorbent article having a first topsheet with a high trans-topsheet penetration overlaying a secondary topsheet having a lesser trans-topsheet penetration.

Accordingly, it is an object of this invention to provide a disposable absorbent article which reduces leakage of fecal material from the disposable absorbent article and minimizes the amount of low-viscosity fecal material remaining on the skin of the wearer once the disposable absorbent article is removed. It is further an object of this invention to provide a disposable absorbent article which separates the fecal material into components.

SUMMARY OF THE INVENTION

The present invention is directed to a disposable absorbent article. The disposable absorbent article comprises a liquid pervious topsheet, a backsheet joined to the topsheet, and a fecal management member positioned between the topsheet and the backsheet. The fecal management member comprises a backing and a sheet of fibers. The sheet of fibers have anchor portions in the backing at spaced bonding locations and have arcuate portions of the sheet projecting from the backing between bonding locations.

The disposable absorbent article preferably comprises an absorbent core which is positioned between the fecal management member and the backsheet.

BRIEF DESCRIPTION OF THE DRAWINGS

While the specification concludes with claims particularly pointing out and distinctly claiming the subject matter which is regarded as the present invention, it is believed that the description will be better understood from the following descriptions which are taken in conjunction with the accompanying drawings in which like designations are used to designate substantially identical elements.

DETAILED DESCRIPTION OF THE INVENTION

As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused. as an absorbent article (i.e., they are intended to be discarded after a single use and, preferably, to be recycled, composted or otherwise disposed of in an environmentally compatible manner). (As used herein, the term "disposed" is used to mean that an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons about the lower torso. The present invention is also applicable to other absorbent articles such as incontinence briefs, incontinence undergarments, absorbent inserts, diaper holders and liners, feminine hygiene garments, and the like.

Figure 1:
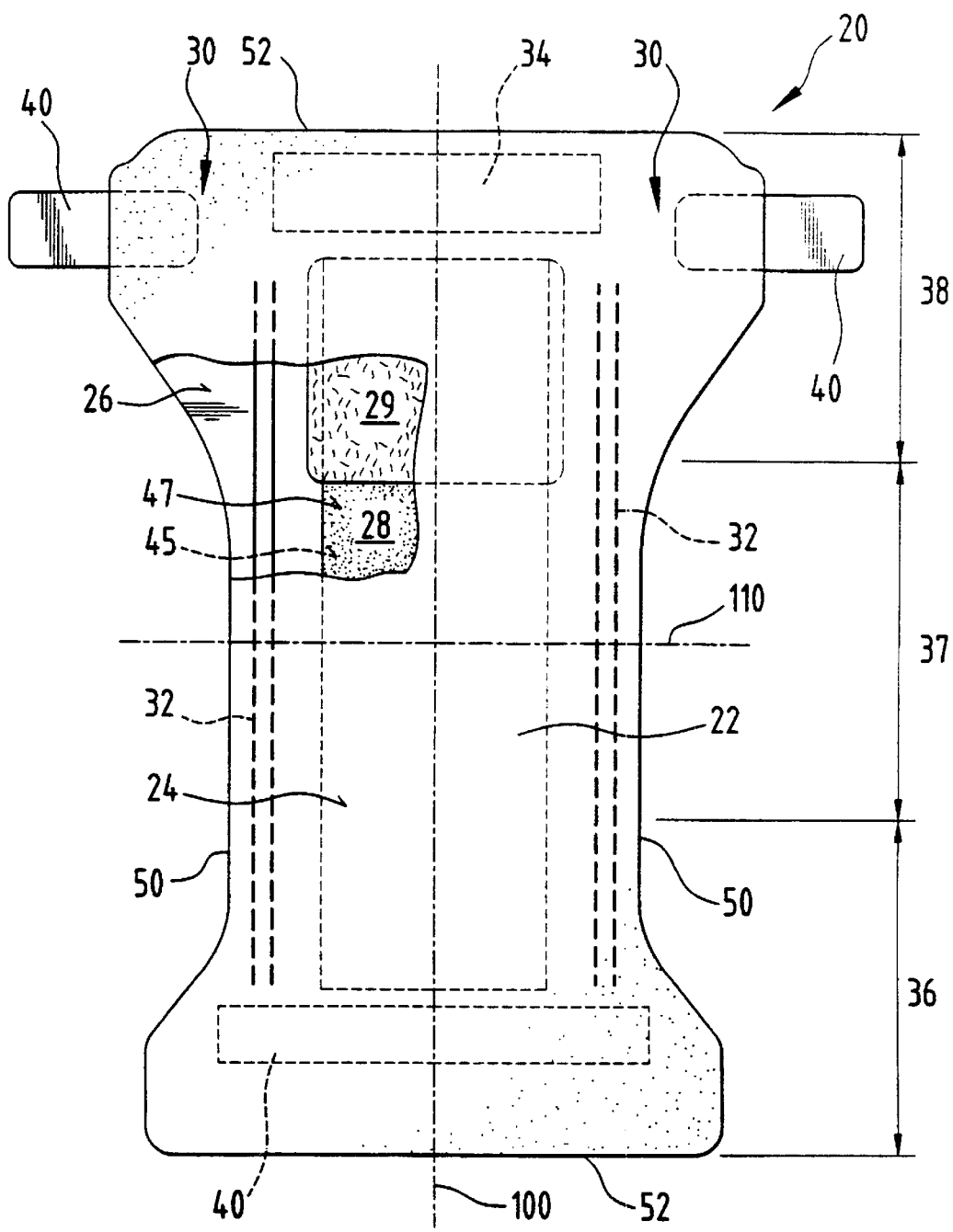
FIG. 1 is a plan view of an absorbent article embodiment of the present invention having portions cut away to reveal the underlying structure, the garment-facing surface of the diaper facing the viewer.

FIG. 1 is a plan view of the diaper 20 of the present invention in a flat-out, state with portions of the structure being cut-away to more clearly show the construction of the diaper 20. The portion of the diaper 20 which faces the wearer is oriented towards the viewer. As shown in FIG. 1, the diaper 20 preferably comprises a liquid pervious topsheet 24; a liquid impervious backsheet 26; an absorbent core 28, which is preferably positioned between at least a portion of the topsheet 24 and the backsheet 26; a fecal management member 29 positioned between the topsheet 24 and the absorbent core 28; side panels 30; elasticized leg cuffs 32; an elastic waist feature 34; and a fastening system generally designated 40. Diaper 20 is shown in FIG. 1 to have a front waist region 36, a rear waist region 38 opposed to the front waist region 36 and a crotch region 37 located between the front waist region and the rear waist region. The periphery of the diaper 20 is defined by the outer edges of the diaper 20 in which the longitudinal edges 50 run generally parallel to the longitudinal centerline 100 of the diaper 20 and the end edges 52 run between the longitudinal edges 50 generally parallel to the lateral centerline 110 of the diaper 20.

The chassis 22 of the diaper 20 comprises the main body of the diaper 20. The chassis 22 comprises at least a portion of the absorbent core 28 and preferably an outer covering layer including the topsheet 24 and the backsheet 26. If the absorbent article comprises a separate holder and a liner, the chassis 22 generally comprises the holder and the liner. (For example, the holder may comprise one or more layers of material to form the outer cover of the article and the liner may comprise an absorbent assembly including a topsheet, a backsheet, and an absorbent core. In such cases, the holder and/or the liner may include a fastening element which is used to hold the liner in place throughout the time of use.) For unitary absorbent articles, the chassis 22 comprises the main structure of the diaper with other features added to form the composite diaper structure. While the topsheet 24, the backsheet 26, and the chassis 22 may be assembled in a variety of well known configurations, preferred diaper configurations are described generally in U.S. Pat. No. 3,860, 003 entitled "Contractible Side Portions for Disposable Diaper" which issued to Kenneth B. Buell on Jan. 14, 1975; and U.S. Pat. No. 5,151,092 issued to Buell on Sep. 9, 1992; and U.S. Pat. No. 5,221,274 issued to Buell on Jun. 22, 1993. Other suitable diaper chassis design are disclosed in U.S. Pat. No. 5,569,232 entitled "Absorbent Article With Multiple Zone Structural Elastic-Like Film Web Extensible Waist Feature" which issued to Roe et al. on Oct. 29, 1996; U.S. Pat. No. 5,554,144 entitled "Absorbent Article With Multiple Zone Structural Elastic-Like Film Web Extensible Waist Feature" which issued to Roe et al. on Sep. 10, 1996; U.S. Pat. No. 5,554,143 entitled "Absorbent Article With Multiple Zone Structural Elastic-Like Film Web Extensible Waist Feature" which issued to Roe et al. on Sep. 10, 1996; U.S. Pat. No. 5,554,145 entitled "Absorbent Article With Multiple Zone Structural Elastic-Like Film Web Extensible Waist Feature" which issued to Roe et al. on Sep. 10, 1996; U.S. Pat. No. 5,556,394 entitled "Absorbent Article With Multiple Zone Structural Elastic-Like Film Web Extensible Waist Feature" which issued to Roe et al. on Sep. 17, 1996. Each of these references is hereby incorporated by reference herein.

The backsheet 26 is generally that portion of the diaper 20 positioned adjacent the garment facing surface 45 of the absorbent core 28 which prevents the exudates absorbed and contained therein from soiling articles which may contact the diaper 20, such as bedsheets and undergarments. In preferred embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962 and X10964. Other suitable backsheet materials may include breathable materials which permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont and copending U.S. patent application Ser. No. 08/744,487, filed on Nov. 6, 1996 in the name of Curro. Other breathable backsheets including nonwoven webs and apertured formed films are described in U.S. Pat. No. 5,571,096 issued to Dobrin et al. on Nov. 5, 1996. Each of these references is hereby incorporated by reference herein.

The backsheet 26, or any portion thereof, may be elastically extensible in one or more directions. In one embodiment, the backsheet 26 may comprise a structural elastic-like film ("SELF") web. A structural elastic-like film web is an extensible material that exhibits an elastic-like behavior in the direction of elongation without the use of added elastic materials. The SELF web includes a strainable network having at least two contiguous, distinct, and dissimilar regions. Preferably, one of the regions is configured so that it will exhibit resistive forces in response to an applied axial elongation in a direction parallel to the predetermined axis before a substantial portion of the other region develops significant resistive forces to the applied elongation. At least one of the regions has a surface-pathlength which is greater than that of the other region as measured substantially parallel to the predetermined axis while the material is in an untensioned condition. The region exhibiting the longer surface-pathlength includes one or more deformations which extend beyond the plane of the other region. The SELF web exhibits at least two significantly different stages of controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-pathlength to enter the plane of applied elongation, whereupon the SELF web exhibits second resistive forces to further elongation. The total resistive forces to elongation are higher than the first resistive forces to elongation provided by the first region. SELF webs suitable for the present invention are more completely described in U.S. Pat. No. 5,518,801 entitled Web Materials Exhibiting ElasticLike Behavior, which issued to Chappell, et, al. on May 21, 1996, which is incorporated herein by reference. In alternate embodiments, the backsheet 26 may comprise elastomeric films, foams, strands, or combinations of these or other suitable materials with nonwovens or synthetic films.

The backsheet 26 may be joined to the topsheet 24, the absorbent core 28 or any other element of the diaper 20 by any attachment means known in the art. For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986 entitled "Disposable WasteContainment Garment", which issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Adhesives which have been found to be satisfactory are manufactured by H. B. Fuller Company of St. Paul, Minn. and marketed as HL-1258. Alternatively, the attachment means may comprise heat bonds, pressure bonds, ultrasonic bonds, dynamic mechanical bonds, or any other suitable attachment means or combinations of these attachment means as are known in the art.

The topsheet 24 is preferably positioned adjacent the body surface 47 of the absorbent core 28 and may be joined thereto and/or to the backsheet 26 by any attachment means known in the art. Suitable attachment means are described above with respect to means for joining the backsheet 26 to other elements of the diaper 20. In one preferred embodiment of the present invention, the topsheet 24 and the backsheet 26 are joined directly to each other in some locations and are indirectly joined together in other locations by directly joining them to other elements of the diaper 20.

The topsheet 24 is preferably compliant, soft feeling, and non-irritating to the wearer's skin. Further, at least a portion of the topsheet 24 is liquid pervious, permitting liquids to readily penetrate through its thickness. A suitable topsheet 24 may be manufactured from a wide range of materials, such as porous foams; reticulated foams; apertured plastic films; woven or nonwoven webs of natural fibers (e.g., wood or cotton fibers), synthetic fibers (e.g., polyester or polypropylene fibers), or a combination of natural and synthetic fibers; or apertured nonwoven webs. If the absorbent assemblies include fibers, the fibers may be spunbond, carded, wet-laid, meltblown, hydroentangled, or otherwise processed as is known in the art. One suitable topsheet 24 comprising a web of staple length polypropylene fibers is manufactured by Veracity, Inc., a Division of International Paper Company, of Walpole, Mass. under the designation P-8.

Suitable formed film topsheets are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. Other suitable topsheets 30 are made in accordance with U.S. Pat. Nos. 4,609,518 and 4,629,643 which issued to Curro et al. on Sep. 2, 1986 and Dec. 16, 1986, respectively, and both of which are incorporated herein by reference. Such formed films are available from The Procter & Gamble Company of Cincinnati, Ohio as "DRI-WEAVE" and from Tredegar Corporation of Terre Haute, Ind. as "CLIFF-T."

Preferably, the topsheet 24 is made of a hydrophobic material or is treated to be hydrophobic in order to isolate the wearer's skin from liquids contained in the absorbent core 28. If the topsheet 24 is made of a hydrophobic material, preferably at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant or by incorporating a surfactant into the topsheet. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991. A more detailed discussion of some suitable methods for incorporating surfactant in the topsheet can be found in U.S. Statutory Invention Registration No. H1670, published on Jul. 1, 1997 in the names of Aziz et al. Each of these references is hereby incorporated by reference herein.

Any portion of the topsheet 24 may be coated with a lotion as is known in the art. Examples of suitable lotions include those described in U.S. Pat. No. 5,607,760 entitled "Disposable Absorbent Article Having A Lotioned Topsheet Containing an Emollient and a Polyol Polyester Immobilizing Agent" which issued to Roe on Mar. 4, 1997; U.S. Pat. No. 5,609,587 entitled "Diaper Having A Lotioned Topsheet Comprising A Liquid Polyol Polyester Emollient And An Immobilizing Agent" which issued to Roe on Mar. 11, 1997; U.S. Pat. No. 5,635,191 entitled "Diaper Having A Lotioned Topsheet Containing A Polysilozane Emollient" which issued to Roe et al. on Jun. 3, 1997; and U.S. Pat. No. 5,643,588 entitled "Diaper Having A Lotioned Topsheet" which issued to Roe et al. on Jul. 1, 1997. The topsheet may also include or be treated with antibacterial agents, some examples of which are disclosed in PCT Publication No. WO 95/24173 entitled "Absorbent Articles Containing Antibacterial Agents in the Topsheet For Odor Control" which was published on Sep. 14, 1995 in the name of Johnson. Further, the topsheet 24, the backsheet 26 or any portion of the topsheet or backsheet may be embossed and/or matte finished to provide a more cloth like appearance.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core(s) or other absorbent structure(s) may have varying caliper zones, a hydrophilic gradient, a superabsorbent gradient, or lower average density and lower average basis weight acquisition zones, or may comprise one or more layers or structures). However, the total absorbent capacity of the absorbent core 28 should be compatible with the design loading and the intended use of the diaper 20.

Exemplary absorbent structures for use as the absorbent assemblies are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; and U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994. Each of these patents is incorporated herein by reference.

Figure 2:
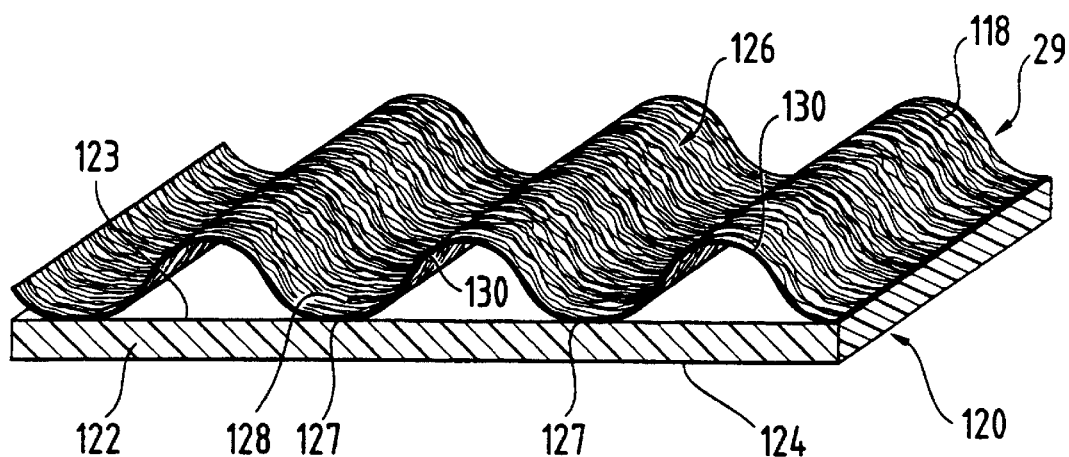
FIG. 2 is a perspective illustration of a fecal management member of the present invention.

FIG. 2 illustrates a first embodiment of a fecal management member according to the present invention, generally designated by the reference numeral 29. Generally the fecal management member 29 is a sheet of loop material 118 having a backing 120 preferably comprising a thermoplastic backing layer 122 (e.g., of polypropylene) having front and rear major surfaces 123 and 124, and a multiplicity of longitudinally oriented fibers in a specially formed sheet of fibers 126 having anchor generally non-deformed anchor portions 127 bonded by being embedded in the backing layer 122 at spaced elongate generally parallel bonding locations 128 that are continuous in one direction along the front surface 123 with arcuate portions 130 of the sheet of fibers 126 projecting from the front surface 123 of the backing layer 122 between the bonding locations 128 in continuous rows also extending transversely across the sheet of loop material 118. The arcuate portions 130 of the sheet of fibers 126 have a generally uniform height from the backing layer 122 of greater than about 0.5 millimeters and preferably greater than about 1.0 millimeters, the height of the formed sheet of fibers 126 is at least one third, and preferably one half to one and one half times the distance between the bonding locations 128, the individual fibers in the sheet of fibers 126 are less than 25 denier (preferably in the range of 1 to 10 denier) in size, and the sheet of fibers 126 without the backing 120 has a basis weight in the range of 5 to 300 grams per square meter (and preferably in the range of 15 to 100 grams per square meter) measured along the first surface 123 to provide sufficient open area between the fibers in the sheet of fibers 126 along the arcuate portions 130 (i.e., between about 10 and 90 percent open area) to afford ready penetration of fecal material into the individual fibers along the arcuate portions 130.

Suitable materials for use as the backing 120 include but are not limited to thermoplastic films, porous films, apertured films, apertured formed films, unapertured formed films, nonwoven webs, breathable materials, such as breathable films, including but not limited to microporous films, apertured nonwoven webs and the like. The backing 120 is preferably a relatively thin layer having a thickness in the range of about 0.00125 to 0.025 centimeters.

The fibers in the sheet of fibers 126 can be disposed in various directions with respect to the parallel bonding locations 128 and may or may not be bonded together at crossover points in the arcuate portions 130; can be disposed in various directions with respect to the parallel bonding locations 128 with the majority of the fibers in the sheet of fibers 126 (i.e., over 80 or 90 percent) extending in directions at about a right angle to the bonding locations 128; or all of the individual fibers in the sheet of fibers 126 can extend in directions generally at right angles to the spaced generally parallel bonding locations 128.

Sheet of fibers 126 preferably has a hydrophilicity which is less than the hydrophilicity of the backing 120. In a preferred embodiment, the sheet of fibers themselves have a hydrophilicity gradient wherein the arcuate portions 130 have a hydrophilicity which is less than the hydrophilicity of the bonded locations 128. Even in this configuration it is preferred that the bonded locations 128 of the sheet of fibers 126 have a hydrophilicity which is less than the hydrophilicity of the backing 120.

Preferably the fecal management member 29 is secured to the topsheet 24 in a very minimal extent to preserve the openness of the fecal management member 29 to allow ready penetration of fecal material. More preferably, the fecal management member 29 is not secured to the topsheet 24 at all preserving the openness of the fecal management member 29 and also allowing the topsheet 24 to separate from the fecal management member 29 creating additional void space within the disposable absorbent article. However, it is recognized that the fecal management member 29 should be secured within the diaper 20 to prevent it from freely moving about. To this end, it is preferred that the fecal management member 29 be secured directly to the underlying absorbent core 28. The fecal management member 29 may be joined to the absorbent core 28 by any attachment means known in the art. For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986 entitled "Disposable Waste-Containment Garment", which issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Adhesives which have been found to be satisfactory are manufactured by H. B. Fuller Company of St. Paul, Minn. and marketed as HL-1258. Alternatively, the attachment means may comprise heat bonds, pressure bonds, ultrasonic bonds, dynamic mechanical bonds, or any other suitable attachment means or combinations of these attachment means as are known in the art. A particularly preferred attachment means is an adhesive having a hydrophilicity which is greater than the hydrophilicity of the sheet of fibers 126, more preferably a hydrophilicity which is also greater than the hydrophilicity of the backing 120.

The fecal management member 29 is shown in FIG. 1 to be positioned in the rear waist region 38 of the diaper 20. By positioning the fecal management member 29 at least in the rear waist region 38, the fecal management member 29 is aligned with the wearer's anus where it can be most effective in the management of fecal material deposited onto the diaper 20. However, the fecal management member 29 may extend into crotch region 37. The fecal management member 29 may also extend into the front waist region 36 of the diaper 20. In some embodiments it may also be desirable to have the fecal management member 29 extend along the entire longitudinal dimension of the diaper 20.

In addition to positioning the fecal management member 29 at least in the rear waist region 38 it is also desirable that the portion of the topsheet 24 positioned within the rear waist region 38 have a sufficient open area to handle low-viscosity fecal material.

To be the most effective in the handling of low-viscosity fecal material the fecal management member must have a lofted open structure. One key component of this equation is the height of the arcuate portions 130 of the sheet of fibers 126 from the backing 120. As mentioned above the arcuate portions 130 of the sheet of fibers 126 have a generally uniform height from the backing 120 of greater than about 0.5 millimeters and preferably greater than about 1.0 millimeters. While even greater heights would provide excellent handling of low-viscosity fecal material, e.g., heights of 5.0 centimeters, such heights would create unwanted bulk in the diaper which may cause discomfort for the wearer.

The other key component is the resiliency of the fecal management member 29, more particularly the resiliency of the sheet of fibers 126. In order to remain open, the sheet of fibers 126 must have a sufficient resiliency to withstand the forces of packaging and those applied by the wearer. Preferably, the sheet of fibers 126 has a resiliency of at least 50% after 30 seconds under an applied force of 100 g/cm2, more preferably, the sheet of fibers 126 has a resiliency of at least 75% after 30 seconds under an applied force of 100 g/cm2, most preferably, the sheet of fibers 126 has a resiliency of at least 85% after 30 seconds under an applied force of 100 g/cm2.

The anchor portions 127 are preferably of such dimension that a planar circle having a diameter of from about 0.2 millimeters to about 20 millimeters may be inscribed thereon, more preferably, the anchor portions 127 are preferably of such dimension that a planar circle having a diameter of from about 0.4 millimeters to about 10 millimeters may be inscribed thereon, and most preferably, the anchor portions 127 are preferably of such dimension that a planar circle having a diameter of from about 0.8 millimeters to about 5 millimeters may be inscribed thereon.

Figure 3:
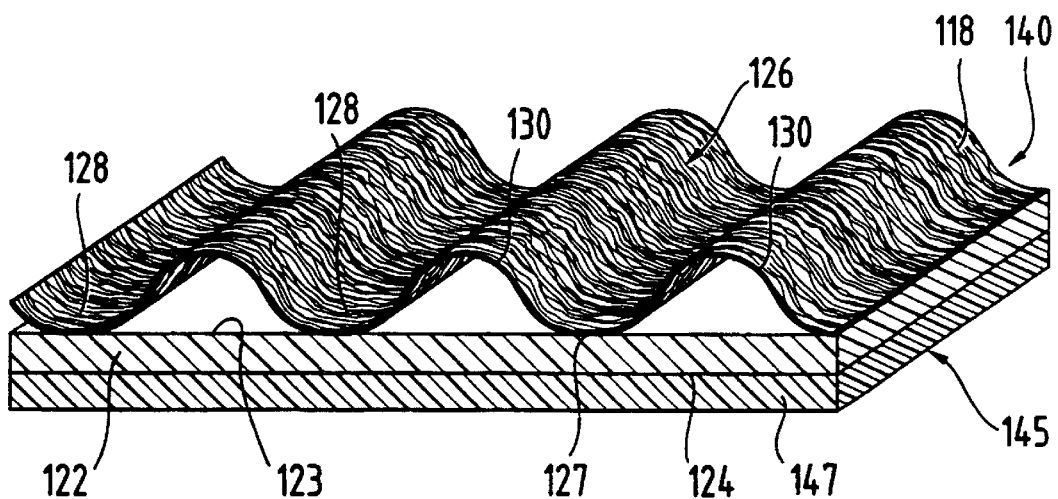
FIG. 3 is a perspective illustration of a second embodiment of a fecal management member of the present invention.

FIG. 3 illustrates a second embodiment of a fecal management member according to the present invention, generally designated by the reference numeral 140, which fecal management member 140 has the same structure as the fecal management member 29 (the same reference numerals being used with respect to the corresponding portions thereof) except that backing 145 of the sheet of loop material 118 includes a second sheet of backing material 147, which second sheet of backing material 147 is adhered on the side 124 of the backing layer 122 opposite the sheet of fibers 126. The second sheet of backing material 147 in the backing 145 of the sheet of loop material 118 may be a polymeric film. Other suitable materials for use as the second sheet of backing material 147 include but are not limited to porous films, apertured films, apertured formed films, unapertured formed films, nonwoven webs, breathable materials, such as breathable films, including but not limited to microporous films, apertured nonwoven webs and the like. The second sheet of backing material 147 is preferably a relatively thin layer having a thickness in the range of about 0.00125 to 0.025 centimeters.

Figure 4:
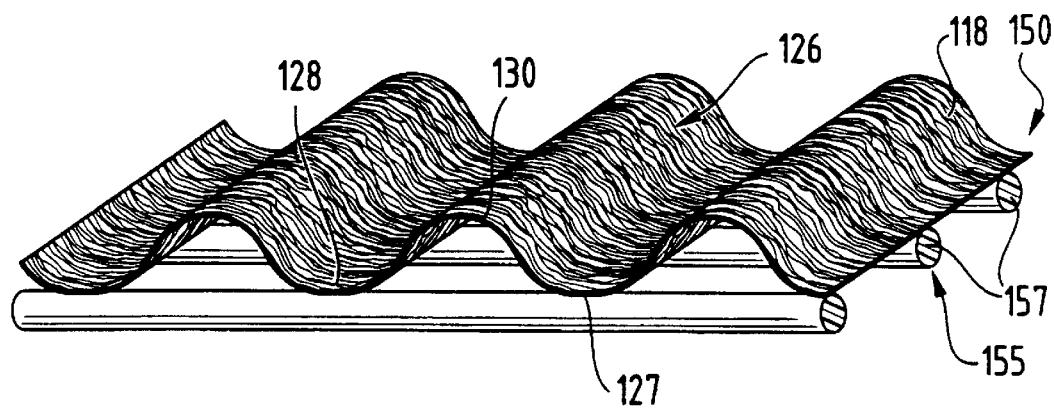
FIG. 4 is a perspective illustration of a third embodiment of a fecal management member of the present invention.

FIG. 4 illustrates a third embodiment of a fecal management member according to the present invention, generally designated by the reference numeral 150, which fecal management member 150 has the same structure as the fecal management member 29 (the same reference numerals being used with respect to the corresponding portions thereof) except that backing 155 of the sheet of loop material 118 includes a plurality of fibers 157. Fibers 157 of backing 155 can be disposed in various directions with respect to the parallel bonding locations 128 and may or may not be bonded together, can be disposed in various directions with respect to the parallel bonding locations 128 with the majority of the fibers in the backing 155 (i.e., over 80 or 90 percent) extending in directions at about a right angle to the bonding locations 128; or all of the individual fibers 157 in the backing 155 can extend in directions generally at right angles to the spaced generally parallel bonding locations 128. Preferably, the individual fibers 157 are not bonded together and are spaced from one another by a distance of from about 0.01 mm to about 10.0 mm. The fibers 157 have a denier within the range of about 0–50.

Figure 5:
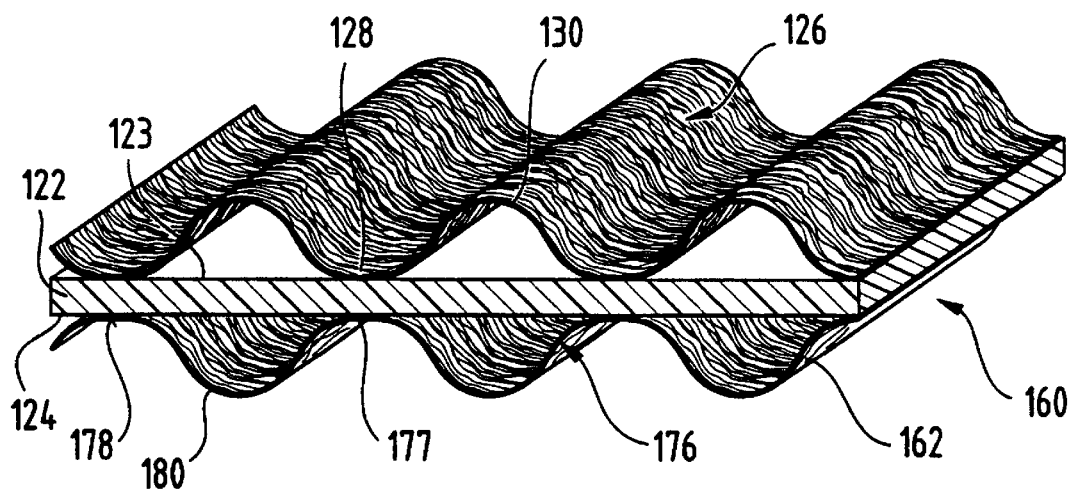
FIG. 5 is a perspective illustration of a fourth embodiment of a fecal management member of the present invention.

FIG. 5 illustrates a fourth embodiment of a fecal management member according to the present invention, generally designated by the reference numeral 160, which fecal management member 160 has the same structure as the fecal management member 29 (the same reference numerals being used with respect to the corresponding portions thereof) except that fecal management member 160 includes a second sheet of loop material 162 which second sheet of loop material 162 is adhered on the side 124 of the backing layer 122 opposite the sheet of fibers 126. The second sheet of loop material 162 comprises a multiplicity of longitudinally oriented fibers in a specially formed sheet of fibers 176 having anchor generally non-deformed anchor portion 177 bonded by being embedded in the backing layer 122 at spaced elongate generally parallel bonding locations 178 that are continuos in one direction along the surface 124 with arcuate portions 180 of the sheet of fibers 176 projecting from the surface 124 of the backing layer 122 between the bonding locations 178 in continuous rows also extending transversely across the sheet of loop material 162. The arcuate portions 180 of the sheet of fibers 176 have a generally uniform height from the backing layer 122 of greater than about 0.5 millimeters and preferably greater than about 1.0 millimeters, the height of the formed sheet of fibers 176 is at least one third, and preferably one half to one and one half times the distance between the bonding locations 178, the individual fibers in the sheet of fibers 176 are less than 25 denier (preferably in the range of 1 to 10 denier) in size, and the sheet of fibers 176 without the backing 120 has a basis weight in the range of 5 to 300 grams per square meter (and preferably in the range of 15 to 100 grams per square meter) measured along the first surface 124.

In the embodiment shown in FIG. 5 the bonding locations 128 and 178 are aligned with one another, i.e., bonding location 128 positioned directly above bonding location 178, causing the arcuate portions 130 and 180 to be in phase. The bonding locations 128 and 178 may also be positioned along the backing 120 such that they are not aligned with one another causing the arcuate portions 130 and 180 to be out of phase.

Figure 6:
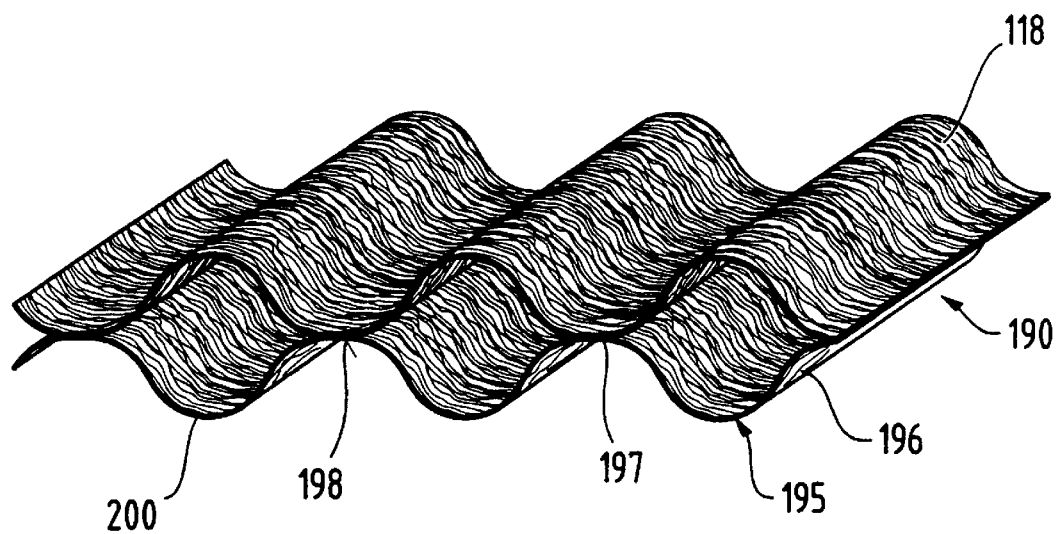
FIG. 6 is a perspective illustration of a fifth embodiment of a fecal management member of the present invention.

FIG. 6 illustrates a fifth embodiment of a fecal management member according to the present invention, generally designated by reference numeral 190, which fecal management member 190 has the same structure as the fecal management member 29 (the same reference numerals being used with respect to the corresponding portions thereof) except that the backing 195 of the sheet of loop material 118 is a sheet of loop material 196 which is adhered directly to loop material 118. The sheet of loop material 196 comprises a multiplicity of longitudinally oriented fibers in a specially formed sheet of fibers having anchor generally non-deformed anchor portion 197 bonded by being thermo-bonded to the loop material 118 at spaced elongate generally parallel bonding locations 198 arcuate portions 200 of the sheet of fibers 196 projecting from the anchor portions 197 in continuous rows also extending transversely across the sheet of loop material 196.

In the embodiment of FIG. 6, the rows of arcuate portions of the sheet of loop material 118 and 196 extend parallel to one another in the transverse direction. Alternatively, the rows of arcuate portions of the sheet of loop material 118 and 196 may be nonparallel. For example, the rows of arcuate portions of the sheet of loop material 118 may extend in the transverse direction while the rows of arcuate portions of the sheet of loop material 196 extend at an angle to the transverse direction.

Figure 7:
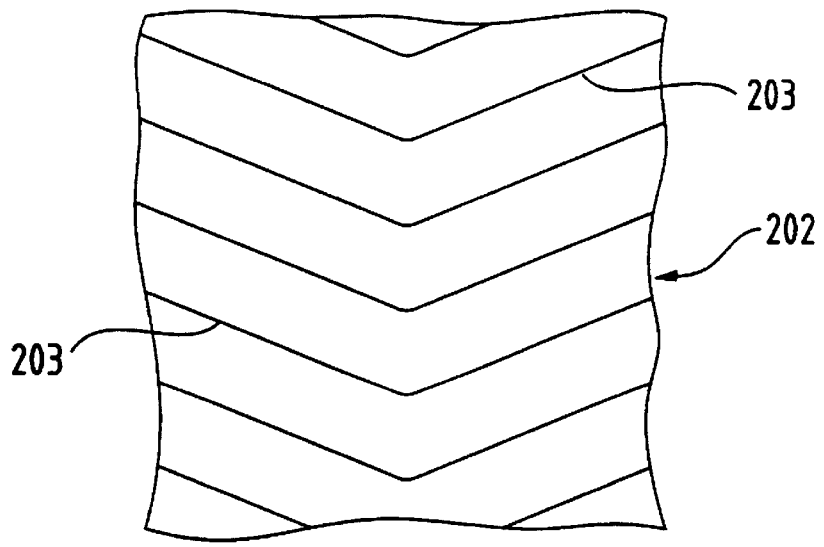
FIG. 7 is a plan view illustration of another embodiment of a fecal management member of the present invention.

FIG. 7 is a top plan view of another embodiment of a fecal management member 202 of the present invention. Fecal management member 202 depicts one of many possible configuration for the arrangement of the rows of arcuate portions 203.

Figure 8:
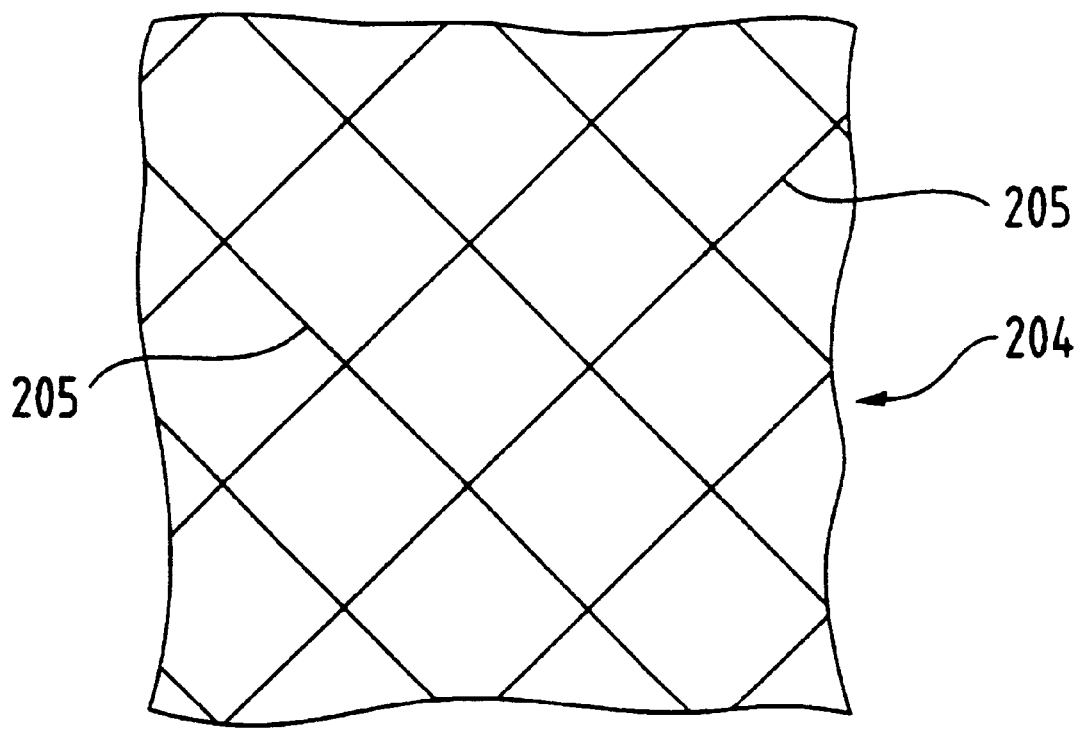
FIG. 8 is a plan view illustration of another embodiment of a fecal management member of the present invention.

FIG. 8 is a top plan view of another embodiment of a fecal management member 204 of the present invention. Fecal management member 204 depicts one of many possible configuration for the arrangement of the rows of arcuate portions 205.

In addition to the configurations shown in FIGS. 7 and 8, other possible configurations for the arrangement of the rows of arcuate portions may also be used.

Figure 9:
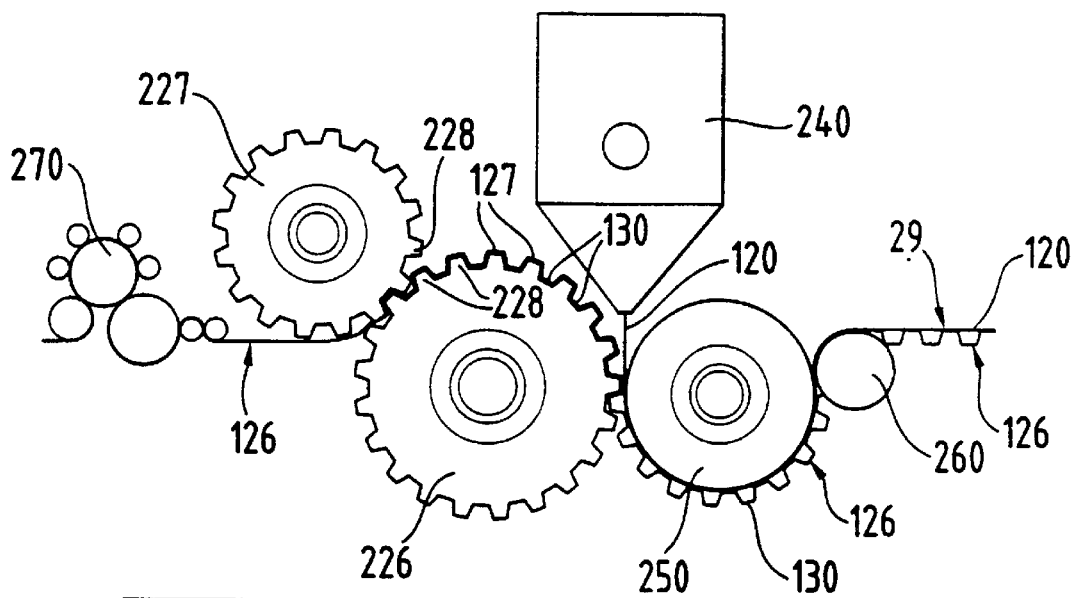
FIG. 9 is a schematic illustration of a method and equipment for making the fecal management member of the present invention.

FIG. 9 schematically illustrates a method and equipment for forming the fecal management member 29. The method illustrated in FIG. 9 generally comprises forming longitudinally oriented polymeric fibers into a sheet of fibers 126, forming the sheet of fibers 126 so that it has arcuate portions 130 projecting in the same direction from the spaced generally parallel anchor portions 127 of the sheet of fibers 126, and bonding the spaced generally parallel anchor portions 127 of the sheet of fibers 126 projecting from the front surface 123 of the backing 120. This method is performed by providing first and second heated corrugating members or rollers 226 and 227 each having an axis and including a plurality of circumferentially spaced generally axially extending ridges 228 around and defining its periphery, with the ridges 228 having outer surfaces and defining spaces between the ridges 228 adapted to receive portions of the ridges 228 of the other corrugating member 226 or 227 in meshing relationship with the sheet of fibers 126 between the meshed ridges 228 and to afford rolling engagement between the ridges 228 and spaces of the corrugating members in the manner of gear teeth. The corrugating members 226 and 227 are mounted in axially parallel relationship with portions of the ridges 228 of the corrugating members 226 and 27 meshing generally in the manner of gear teeth; at least one of the corrugating members 226 or 227 is rotated; and the sheet of fibers 126 is fed between the meshed portions of the ridges 228 of the corrugating members 226 and 227 to generally conform the sheet of fibers 126 to the periphery of the first corrugating member 226 and form the arcuate portions 130 of the sheet of fibers 126 in the spaces between the ridges 228 of the first corrugating member 226 and the generally parallel anchor portions 127 of the sheet of fibers 126 along the outer surfaces of the ridges 228 on the first corrugating member 226. The formed sheet of fibers 126 is retained along the periphery of the first corrugating member 226 after it has moved past the meshed portions of the ridges 228. The thermoplastic backing layer 120 is formed and bonded to the anchor portions 127 of the sheet of fibers 126 on the end surfaces of the ridges 228 on the first corrugating member 226 by extruding the thermoplastic backing layer 120 (e.g., polypropylene) in a molten state from a die 240 into a nip between the anchor portions 127 of the sheet of fibers 126 on the periphery of the first corrugating member 226 and a cooling roll 250 after which the fecal management member 29 is separated from the first corrugating member 226 and carried partially around the cooling roll 250 and through a nip between the cooling roller and a pinch roller 260 to complete cooling and solidification of the thermoplastic backing layer 120.

The sheet of fibers 126 fed between the meshed portions of the ridges 228 of the corrugating members 226 and 227 can be in the form of yarns distributed so that the fibers in the sheet of fibers 126 fed between the meshed ridges 228 of the corrugating members 226 and 227 are uniformly distributed across the width of the sheet of fibers 126 and all extend generally perpendicular to the axes of the corrugating members 226 and 227, or the fibers in the sheet of fibers 126 can be disposed in random orientation as in a non woven web or sheet. Such a nonwoven sheet of randomly oriented fibers 126 with no internal bonding except for the friction between the fibers can be formed from loose fibers using a carding machine 270 as illustrated, which nonwoven sheet of randomly oriented fibers 126 has enough integrity to be fed from the carding machine 270 into the nip between the corrugating members 226 and 227 (if needed, a conveyer (not shown) could be provided to help support and guide the non woven sheet of randomly oriented fibers 126 is used, preferably the first corrugating member 226 has a rough finish (e.g., formed by sand blasting), the second corrugating member 227 has a smooth polished finish, and the first corrugating member 226 is heated to a temperature slightly above the temperature of the second corrugating member 226 so that the nonwoven sheet of fibers 126 will preferentially stay along the surface of the first corrugating member 226 and be carried to the nip between the first corrugating member and the cooling roller 250 after passing through the nip between the corrugating members 226 and 227.

Corrugating members 226 and 227 adapted to have such a sheet of fibers 126 fed into them can have their ridges 228 oriented generally in the range of 0 to 90 degrees with respect to their axes, but preferably have their ridges 228 oriented at 0 degrees with respect to (or parallel to) their axes which simplifies making of the corrugating members 226 and 227.

Instead of extruding a solid thermoplastic sheet 120 from die 240, a plurality of fibers may be extruded from a die to form a backing layer, such as backing layer 155 illustrated in FIG. 4.

Instead a extruding a thermoplastic material from a die such as die 240, a non-molten backing maybe used. The roller 250 is then heated to thermo-bond the backing to the sheet of fibers.

Figure 10:
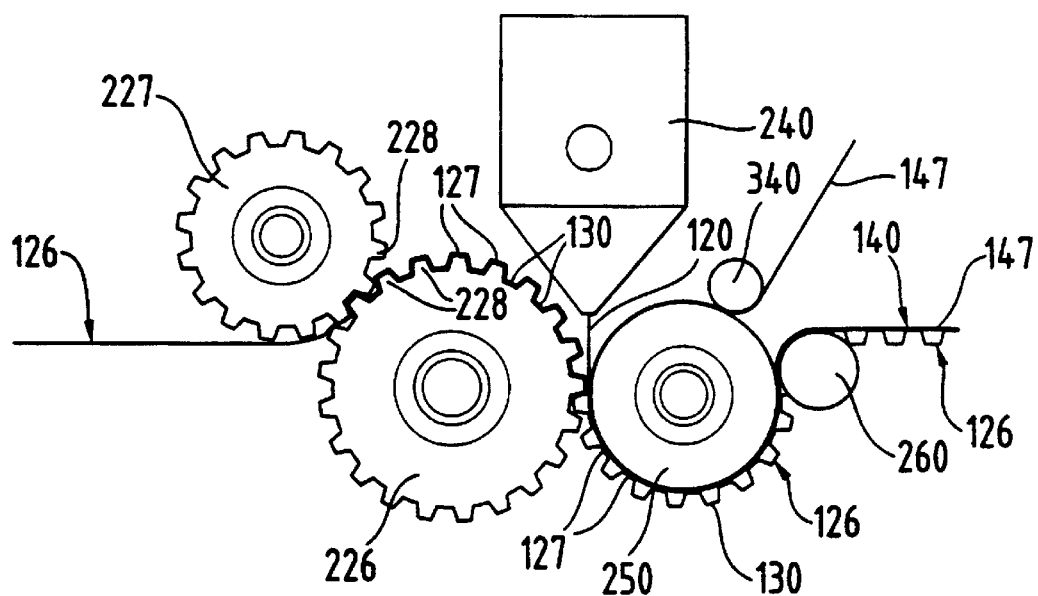
FIG. 10 is a schematic illustration of another embodiment of a method and equipment for making the fecal management member of the present invention.

FIG. 10 schematically illustrates another embodiment of a method and equipment according to the present invention for forming the fecal management member 140, which method is generally the same and uses much of the same equipment as is illustrated in FIG. 9 (with similar portions of that equipment having the same reference numerals), except for the addition of means including a pinch roller 340 for feeding the sheet of backing material 147 into the nip between the first corrugating roller 226 and the cooling roller 250 along the surface of the cooling roller 250 which results in the extruded molten thermoplastic backing layer 120 from the die 240 being deposited between the formed sheet of fibers 126 along the periphery of the first corrugating member 226 and the sheet of backing material 120 along the surface of the cooling roll 250 so that the molten thermoplastic backing layer 120 envelopes and adheres the anchor portions 127 of the sheet of fibers 126 to the sheet of backing material 147 after which the fecal management member 140 is separated from the first corrugating member 226 and carried partially around the cooling roll 250 with its backing 145 against the cooling roll 250 to complete cooling and solidification of its thermoplastic backing layer 120. The molten thermoplastic backing layer 120 can be extruded into the nip, onto the anchor portions 127 of the sheet of fibers on the first corrugating member 226 prior to the nip, or onto the sheet of backing material 147 along the periphery of the cooling roller just prior to the nip as may work best for any given application. The cooling roll 250 can be water cooled and have a chrome plated periphery which is particularly useful for forming the fecal management member 140 because of the high rate of heat transfer such a cooling roll 250 affords from the molten thermoplastic backing layer 120, through the sheet of polymeric backing material 147 and into the cooling roll 250. Alternatively, the cooling roll 250 may have an outer rubber layer defining its surface which may be preferred for forming the fecal management member 140 if the sheet of backing material is of a material (e.g., paper) that tends to restrict such heat transfer into the cooling roll 250, whereupon the rubber layer provides an alternative advantage of deforming adjacent its nip with the first corrugating roller 226 to provide intimate contact of the molten thermoplastic backing layer 120 with the anchor portions 127 of the sheet of fibers 126 and the sheet of backing material 147.

The sheet of backing material 147 incorporated in the backing 145 could be a woven, knitted, random woven, needle punched, nonwoven or other solid or porous layer of intertwined fibers, or could be a continuous polymeric film. Such film used for the sheet of backing material 21 may be a single layer of a polymeric material such as polypropylene, polyester, or polyamide; or may have a plurality of layers such as a central layer of a relatively high strength material such as polyester, a layer defining the first surface of a material more easily bonded to the layer of thermoplastic material 120 such as ethylene vinyl acetate or polyethylene, and a layer defining the outer surface of the backing 147 adapted to adhere the backing to a substrate such as polyethylene or a bonding layer of room-temperature non-tacky thermoplastic material. The sheet of backing material could also be a layer of pressure sensitive adhesive along a release liner disposed so that the release liner contacts the cooling roller 250, resulting in the layer of pressure sensitive adhesive being disposed alone the rear surface of the layer of thermoplastic material 120 with the release liner over the layer of pressure sensitive adhesive and removable so that the pressure sensitive adhesive could be used to adhere the fecal management member to a substrate.

Preferably, the drives for the corrugating member 226 and 227 and for the cooling roller 250 are separately controllable so that the cooling roller 250 can be rotated at a surface speed that is the same as or different than the surface speed of the first corrugating member 226. When the cooling roller 250 and the first corrugating member 226 are rotated so that they have the same surface speed, the sheet of fibers 126 will have about the same shape along the backing 120 as it had along the periphery of the first corrugating member 226 as is illustrated in FIGS. 2 through 5. When the cooling roller 250 and the first corrugating member 226 are rotated so that the cooling roller has a surface speed that is slower than the surface speed of the first corrugating member 226 the anchor portions 127 of the sheet of fibers 126 will be moved closer together in the backing layer 120 at the nip between the cooling roller 250 and the first corrugating member 226, resulting in greater density of the loop portions 130 along the backing 120 than when the cooling roller 250 and the first corrugating member 226 are rotated so that they have the same surface speed. This technique of increasing the amount of loop portions 130 or the loop population is useful both to make fecal management members having different numbers of loop portions 130 per centimeter of backing length using the same equipment, and to make fecal management members with more loop portions 130 per centimeter of backing length than could be formed between ridges 228 machined on the corrugating member 226 and 227 because of physical limitations in machining such ridges 228 close together.

The diaper 20 may also comprise at least one elastic waist feature 34 that helps to provide improved fit and containment. The elastic waist feature 34 is generally intended to elastically expand and contract to dynamically fit the wearer's waist. The elastic waist feature 34 preferably extends at least longitudinally outwardly from at least one waist edge 62 of the absorbent core 28 and generally forms at least a portion of the end edge 52 of the diaper 20. Disposable diapers are often constructed so as to have two elastic waist features, one positioned in the first waist region 36 and one positioned in the second waist region 38. Further, while the elastic waist feature 34 or any of its constituent elements may comprise one or more separate elements affixed to the diaper 20, the elastic waist feature 34 may be constructed as an extension of other elements of the diaper 20, such as the backsheet 26, the topsheet 24, or both the backsheet 26 and the topsheet 24.

The elastic waist feature 34 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No. 5, 151,092 issued to Buell on Sep. 9, 1992; and U.S. Pat. No. 5,221,274 issued to Buell on Jun. 22, 1993. Other suitable waist configurations may include waistcap features such as those described in U.S. Pat. No. 5,026,364 issued to Robertson on Jun. 25, 1991 and U.S. Pat. No. 4,816,025 issued to Foreman on Mar. 28, 1989. All of the above mentioned references are incorporated herein by reference.

The diaper 20 may also include a fastening system 40. The fastening system 40 preferably maintains the first waist region 36 and the second waist region 38 in an overlapping configuration so as to provide lateral tensions about the circumference of the diaper 20 to hold the diaper 20 on the wearer. The fastening system 40 preferably comprises tape tabs and/or hook and loop fastening components, although any other known fastening means are generally acceptable. Some exemplary fastening systems are disclosed in U.S. Pat. No. 3,848,594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; U.S. Pat. No. 4,846,815 entitled "Disposable Diaper Having An Improved Fastening Device"

issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; and the herein before referenced U.S. Pat. No. 5,151, 092 issued to Buell on Sep. 9, 1992; and U.S. Pat. No. 5, 221,274 issued to Buell on Jun. 22, 1993. The fastening system may also provide a means for holding the article in a disposal configuration as disclosed in U.S. Pat. No. 4,963, 140 issued to Robertson et al. on Oct. 16, 1990. Each of these patents is incorporated herein by reference.

The diaper 20 may also comprise side panels 30. The side panels 30 may be elastic or extensible to provide a more comfortable and contouring fit by initially conformably fitting the diaper 20 to the wearer and sustaining this fit throughout the time of wear well past when the diaper 20 has been loaded with exudates since the elasticized side panels 30 allow the sides of the diaper 20 to expand and contract. The side panels 30 may also provide more effective application of the diaper 20 because even if the diaperer pulls one elasticized side panel 30 farther than the other during application, the diaper 20 will "self-adjust" during wear.

While the diaper 20 of the present invention preferably has the side panels 30 disposed in the second waist region 38, the diaper 20 may be provided with side panels 30 disposed in the first waist region 36 or in both the first waist region 36 and the second waist region 38. The side panels 30 may be constructed in any suitable configurations. Examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151, 092 issued to Buell on Sep. 9, 1992; and U.S. Pat. No. 5, 221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; U.S. patent application Ser. No. 08/155,048 entitled "Absorbent Article With Multi-Directional Extensible Side Panels" filed Nov. 19, 1993 in the names of Robles, et al.; each of which is incorporated herein by reference.

The diaper 20 preferably further includes leg cuffs 32 which provide improved containment of liquids and other body exudates. Leg cuffs may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) which improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs.

The diaper 20 embodiment of the present invention may be applied to a wearer by positioning one of the waist regions, preferably the rear waist region 38, under the wearer's back and drawing the remainder of the diaper 20 between the wearer's legs. The other waist region, preferably the front waist region 36, is positioned across the front of the wearer. The diaperer then wraps the side panels 30 around the wearer such that the front waist region 36 and the rear waist region 38 are in an overlapping configuration. The side panels 30 will typically be extended and tensioned during this operation so as to conform to the size and shape of the wearer. The fastening system 40 is secured to effect a side closure.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising
    a liquid pervious topsheet;
    a backsheet joined to said topsheet; and
    a fecal management member positioned between said topsheet and said backsheet, said fecal management member having a pattern of arcuate portions, wherein the fecal management member has a resiliency of at least 85% after 30 seconds under an applied load of 100 g/cm2.

2. The disposable absorbent article of claim 1 wherein said arcuate portions are formed by a sheet of fibers anchored to a backing at spaced bonding locations such that said sheet of fibers project from said backing in an arcuate manner between bonding locations.

3. The disposable absorbent article according to claim 1 further comprising an absorbent core positioned between said fecal management member and said backsheet.

4. The disposable absorbent article according to claim 2 wherein the backing comprises a plurality of fibers.

5. The disposable absorbent article according to claim 2 wherein the backing comprises a porous film.

6. The disposable absorbent article according to claim 2 wherein the backing comprises a breathable material.

7. The disposable absorbent article according to claim 6 wherein the backing comprises a breathable film.

8. The disposable absorbent article according to claim 2 wherein the backing comprises a nonwoven web.

9. The disposable absorbent article according to claim 8 wherein the backing comprises an apertured nonwoven web.

10. The disposable absorbent article according to claim 2 wherein the arcuate portions have a height from said backing of at least 0.5 mm.

11. The disposable absorbent article according to claim 2 wherein the arcuate portions have a height from said backing of at least 1.0 mm.

12. The disposable absorbent article according to claim 2 further comprising a second backing joined to said backing opposite said sheet of fibers.

13. The disposable absorbent article according to claim 2 wherein said sheet of fibers has a hydrophilicity which is less than the hydrophilicity of said backing.

14. The disposable absorbent article according to claim 2 wherein said anchor portions have a dimension such that a planar circle having a diameter from about 0.2 mm to about 20 mm may be inscribed thereon.

15. The disposable absorbent article according to claim 2 wherein said fecal management member is secured to said absorbent core with a glue having a hydrophilicity which is greater than the hydrophilicity of said sheet of fibers.

16. The disposable absorbent article according to claim 1 wherein said fecal management member is not secured to said topsheet.

17. The disposable absorbent article according to claim 2 wherein the fibers are oriented in the longitudinal direction.

18. The disposable absorbent article according to claim 1 wherein said article has a rear waist region and a front waist region, said fecal management member being positioned in at least said rear waist region of said disposable absorbent article.

19. The disposable absorbent article according to claim 2 further comprising a second sheet of fibers, said second sheet of fibers having anchor portions in said backing opposite said sheet of fibers at spaced bonding locations and having arcuate portions projecting from said backing between bonding locations.

* * * * *

UNITED STATES PATENT AND TRADEMARK OFFICE
CERTIFICATE OF CORRECTION

PATENT NO. : 6,440,114 B1
DATED : August 27, 2002
INVENTOR(S) : Bast et al.

It is certified that error appears in the above-identified patent and that said Letters Patent is hereby corrected as shown below:

Column 4,
Line 31, delete "m ember" and insert therefor -- member --.

Column 6,
Line, 60, delete "ticLike" and insert therefor -- tic-Like --.

Column 7,
Line 7, delete "WasteContainment" and insert therefor -- Waste-Containment --.
Line 47, delete "Veracity" and insert therefor -- Veratec --

Column 14,
Line 22, delete "yams" and insert therefor -- yarns --.

Signed and Sealed this

Fifth Day of April, 2005

JON W. DUDAS
*Director of the United States Patent and Trademark Office*